(12) United States Patent
Schmidt et al.

(10) Patent No.: US 7,247,740 B2
(45) Date of Patent: Jul. 24, 2007

(54) METHOD FOR PRODUCING PERFLUOROALKANE SULFONIC ACID ESTERS AND THE SALTS THEREOF

(75) Inventors: Michael Schmidt, Seeheim-Jugenheim (DE); Nicolai Ignatyev, Duisburg (DE); Udo Heider, Winchester (GB); Peter Sartori, Utting (DE); Andrij Kucheryna, Wuppertal (DE)

(73) Assignee: Merck Patent GmbH, Darmstadt (DE)

( * ) Notice: Subject to any disclaimer, the term of this patent is extended or adjusted under 35 U.S.C. 154(b) by 301 days.

(21) Appl. No.: 10/499,003

(22) PCT Filed: Nov. 25, 2002

(86) PCT No.: PCT/EP02/13222

§ 371 (c)(1),
(2), (4) Date: Jun. 18, 2004

(87) PCT Pub. No.: WO03/053918

PCT Pub. Date: Jul. 3, 2003

(65) Prior Publication Data

US 2005/0085655 A1    Apr. 21, 2005

(30) Foreign Application Priority Data

Dec. 21, 2001 (DE) ................. 101 63 458

(51) Int. Cl.
*C07C 303/00* (2006.01)
*C07C 67/08* (2006.01)
(52) U.S. Cl. ............................ 558/44; 558/53; 558/54; 560/98
(58) Field of Classification Search ................ None
See application file for complete search history.

(56) References Cited

U.S. PATENT DOCUMENTS 5,086,374 A    2/1992    MacFarlane et al.
6,120,707 A *  9/2000    Shirane et al. .............. 252/502

FOREIGN PATENT DOCUMENTS

| JP | 04 233210 | 8/1992 |
| WO | WO 90/14676 | 11/1990 |
| WO | WO 01/15258 | 3/2001 |
| WO | WO 02/098844 | 12/2002 |

OTHER PUBLICATIONS

T. Gramstad, et al.: "Perfluoroalkyl derivatives of sulphur. Part IV. Perfluoroalkanesulphonic acids" Journal of the Chemical Society, Nr.1, 1956.
T.M. Su, et al.: "The solvolysis of highly unreactive substrates using the trifluoromehanesulphonate leaving group" Journal of the American Chemical Society, Bd. 91, Nr.19, Sep. 10, 1969.
Y.Nitta, et al.: "Reaction of carboxylic acid esters with p-toluenesulphonic acid" Chemical and Pharmaceutical Bulletin, Bd.33, Nr. 4, Apr. 1985.
U.Zoller:"The cheletropic fragmentation of hypervalent three-membered thiaheterocyclic intermediates"TEHRAHEDRON, Bd. 44, Nr. 24, Dec. 1988.
D.C.R. Hockless, et al.: "1-Methyl-phenylphosphiranium triflate: synthesis, structure and reactivity" Journal of the Chemical Society, Chemical Communications, Nr. 2, Jan. 21, 1995.
D. Yang, et al.: "Design of efficient ketone catalysts for epoxidation by using the field effect" Journal of Organic Chemistry, Bd. 63, Nr. 24, Oct. 29, 1998.
J.F. King, et al.: "Betylates. 3. Preparative nucleophilic substitution by the way of '2!-'3!-, and '4! Betylates. Stoichiometric phase transfer and substrate-reagent ion-pair (SRIP) reactions of beylates" Journals of the American Chemical Society, Bd. 104, Nr.25, Dec. 15, 1982.
S.E. Denmark, et al.: Catalytic epoxidation of alkenes with oxone Journal of Organic Chemistry, Bd. 60, Nr. 5, 1995.
U. Chiacchio, et al.: "A general synthetic approach to 5-alkyl-2(5H) furanones via 1,3-dipolar cycloaddition" Tetrahedron, Nr. 21, May 21, 1998.
P. Bonhote, et al.: "Hydrophobic, highly conductive ambient-temperature molten salts" Inorganic Chemistry, Bd. 35, Nr. 5, Feb. 28, 1996.
T. Kitazume, et al.: "Preparation of fluorinated alkenes in ionic liquids" Journal of Fluorine Chemistry, Bd. 106, Nr. 2, Dec. 2000.
D.C.R. Hockless, et al.: "Facile syntheses and interconversions between simple phosphiranium and phosphirenium salts" Journal of Organometallic Chemistry, Bd. 529, Nr. 1, Feb. 15, 1997.
H. Heydt, et al.: "Organophosphorus compuounds; 122. Alkylation of 1H-phosphirenes with triflates-synthesis of lambda5, sigma4-1H-phosphirenium cations" Synthesis, Nr. 2, Feb. 1998.
M.L. Di Vona, et al.: "Ring-opening reactions. Part 4. The role of strain and stereochemical effects on the elimination and substitution reactions of small rings; the reactivity of 1,1-dimethylaziridinium systems" Journal of the Chemical Society, Perkin Transactions 2, Nr. 12, Dec. 1985.
K. Rousseau, et al.: "Tetraalkylammonium trifluoromethanesulphonates as supporting electrolytes" Journal of Organic Chemistry, Bd. 37, Nr. 27, Dec. 1, 1972.
Patent Abstracts of Japan, Bd. 016, Nr. 582 (E-1300), Dec. 22, 1992.
B.L. Booth, et al.: "Alkyltrifluoromethanesulphonates as alkylating reagents for aromatic compounds" Journal of the Chemical Society, Perkin Transactions 1, Nr. 12, Dec. 1980.

(Continued)

*Primary Examiner*—Sikarl A. Witherspoon
(74) *Attorney, Agent, or Firm*—Millen, White, Zelano, Branigan, P.C.

(57) ABSTRACT

The present invention relates to a process for the preparation of perfluoroalkanesulfonic acid esters and to the further conversion thereof into salts, and to the use of the resultant compounds in electrolytes and in batteries, capacitors, supercapacitors and electrochemical cells.

17 Claims, No Drawings

OTHER PUBLICATIONS

R.E. Bates, et al.: "Alkylation of enolates with triflates" Journal of Organic Chemistry, Bd. 58, Nr. 16, Jul. 30, 1993.

F. Marcuzzi, et al.: "Vinyl cations in organic synthesis. A new route to disubstituted alkynes" Journal of Organic Chemistry, Bd. 47, Nr. 23, Nov. 5, 1982.

C.D. Beard, et al.: "Synthesis of some novel trifluoromethanesulphonates and their reactions with alcohols" Journal of Organic Chemistry, Bd. 38, Nr. 21, Oct. 19, 1973.

M. Oba, et al.: "Reactions of N-trimethylsilylmethyliminodithiocarbonate with carbonyl compounds: synthetic equivalent of alkylthionitrile ylide" HETEROCYCLES, Bd. 45, Nr. 10, Oct. 1, 1997.

E. Honda, et al.: "Novel ring transformation of dihydroselenines to selenabicyclo'3.1.0!hexenes" HETEROCYCLES, Bd. 55, Nr. 3, Mar. 1, 2001.

* cited by examiner

METHOD FOR PRODUCING PERFLUOROALKANE SULFONIC ACID ESTERS AND THE SALTS THEREOF

The present invention relates to a process for the preparation of compounds containing perfluoroalkanesulfonic acid radicals, in particular the preparation of perfluoroalkanesulfonic acid esters, and to the further conversion thereof into salts, and to the use of the resultant compounds in electrolytes and in batteries, capacitors, supercapacitors and electrochemical cells.

The spread of portable electronic equipment, such as, for example, laptop and palmtop computers, mobile telephones or video cameras, and thus also the demand for lightweight and high-performance batteries has increased dramatically worldwide in recent years. In view of this sudden increase in demand for batteries and the ecological problems associated therewith, the development of rechargeable batteries having a long service life is constantly increasing in importance.

Lithium ion batteries and double-layer capacitors with very high capacities (so-called super- or ultracapacitors) represent the current state of the art. In both systems, hydrolysis-sensitive and thermally unstable substances in the form of $LiPF_6$ or $N(C_2H_5)_4BF_4$ are currently used as conductive salt. In contact with moist air or with residual water from the solvents, HF can form rapidly. Besides the toxic properties, HF has a very adverse effect on the cycle behaviour and thus on the performance of the electrochemical cells.

Alternatives which have been presented are imides, such as bis(trifluoromethylsulfonyl)imide or bis(pentafluoroethylsulfonyl)imide, or methanides, such as tris(trifluoromethylsulfonyl)methanide and derivatives thereof. However, quaternary ammonium and phosphonium salts having perfluoroalkanesulfonate anions have also been developed as conductive salts for electrochemical cells. However, the synthesis of these salts is relatively complex, since an intermediate, methyl trifluoromethanesulfonate (methyl triflate), is difficult to prepare.

There are various synthetic routes to methyl triflate (Gramstad, J. Chem. Soc., 1956, 173-180 or Beard, J. Org. Chem., 1973 (21), 3673-3677). However, none of the synthetic routes described is suitable for scale-up since they either use very toxic starting materials, such as, for example, dimethyl sulfate, the yields are very low, the reaction product has to be purified, or hazardous by-products or waste products are formed, such as, for example, sulfuric acid contaminated with dimethyl sulfate.

The object of the present invention is therefore to overcome the disadvantages of the prior art and to provide a simple and economically effective process for the synthesis of alkyl perfluoroalkanesulfonates and conductive salts which can be prepared therefrom.

This object is achieved by the processes according to claim 1 and claim 9. Special process features are described in sub-claims 2 to 8.

The invention is distinguished by the fact that a perfluoroalkanesulfonic acid is reacted directly with a dialkyl carbonate to give an alkyl perfluoroalkanesulfonate. For example, trifluoromethanesulfonic acid can be reacted directly with dimethyl carbonate. However, the methyl triflate is only formed in low yields (cf. Example 1).

Better yields are obtained in the preferred reaction of a perfluoroalkanesulfonic acid with a dialkyl carbonate in the presence of a water- or alcohol-consuming reagent, such as, for example, a carboxylic acid derivative whose organic radical is stable to perfluoroalkanesulfonic acid, for example

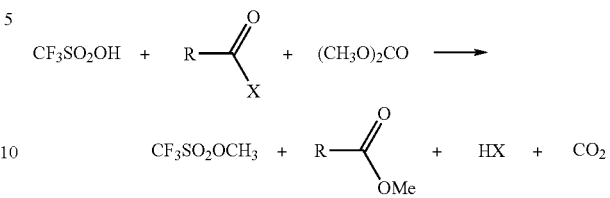

For the purposes of the present invention, a carboxylic acid derivative is a compound in which the hydroxyl group of a carboxylic acid has been replaced by another functional group, for example a halide, a carboxyl radical or a sulfonyl radical. For the purposes of the invention, all carboxylic acid derivatives can in principle be employed so long as their alkyl or aryl radicals—including those containing protons—are stable to perfluoroalkanesulfonic acid.

Surprisingly, the alkylation of the mixture of perfluoroalkanesulfonic acid and carboxylic acid derivative takes place easily and results in good yields of alkylated perfluoroalkanesulfonic acid and carboxylic acid ester. Both compounds can readily be isolated by the person skilled in the art by conventional methods, generally by fractional distillation.

In a preferred embodiment, the carboxylic acid derivatives employed for the process according to the invention are carboxylic acid halides, in particular chlorides, carboxylic anhydrides or mixed carboxylic/sulfonic anhydrides. The use of these starting materials results in good yields of the esters in relatively short reaction times.

The carboxylic acid chloride is particularly preferably selected from the group consisting of: benzoyl chloride, p-nitrobenzoyl chloride, 2,6-difluorobenzoyl chloride, pentafluorobenzoyl chloride, 2-chlorobenzoyl chloride, 3-chlorobenzoyl chloride, 4-chlorobenzoyl chloride, 2-bromobenzoyl chloride, 3-bromobenzoyl chloride, 4-bromobenzoyl chloride, 2,3-dichlorobenzoyl chloride, 2,4-dichlorobenzoyl chloride, 2,6-dichlorobenzoyl chloride, 3,4-dichlorobenzoyl chloride, 3,5-dichlorobenzoyl chloride and trichloroacetyl chloride.

The carboxylic anhydride is particularly preferably benzoic anhydride, 2,2'-dichlorobenzoic anhydride, 3,3'-dichlorobenzoic anhydride, 4,4'-dichlorobenzoic anhydride, 2,2',3,3'-tetrachlorobenzoic anhydride, 2,2',4,4'-tetrachlorobenzoic anhydride, 2,2',6,6'-tetrachlorobenzoic anhydride, 3,3',4,4'-tetrachlorobenzoic anhydride, 3,3',5,5'-tetrachlorobenzoic anhydride, 2-bromobenzoic anhydride, 3-bromobenzoic anhydride, 4-bromobenzoic anhydride or 2,2',6,6'-tetrafluoro-benzoic anhydride.

The dialkyl carbonate used in accordance with the invention by the person skilled in the art can in principle be any known dialkyl carbonate. However, it is preferably selected from the group consisting of dimethyl carbonate, diethyl carbonate, dipropyl carbonate, dibutyl carbonate, methyl ethyl carbonate and mixtures of these dialkyl carbonates.

The process according to the invention is preferably carried out at temperatures between room temperature and 150° C., in particular between 50 and 110° C., very particularly preferably between 70 and 100° C. The preferred reaction time is between 1 and 10 hours, in particular between 2 and 5 hours.

The perfluoroalkanesulfonic acid esters prepared in accordance with the invention can subsequently be converted further into the corresponding perfluoroalkanesulfonic acid salts by reaction with $$XR^1R^2R^3,$$

where
X is P or N,
$R^1$, $R^2$
and $R^3$ are identical or different, are optionally linked directly to one another by a single or double formation and are each, individually or together,
hydrogen
an alkyl radical having from 1 to 16 carbon atoms, which may be partially or fully substituted by further groups, preferably by F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ where $1 \leq n \leq 6$ and $0 \leq x \leq 2n+1$, an unsubstituted or substituted aryl radical or an unsubstituted or substituted aromatic heterocyclic radical,
an alkylaryl radical whose alkylene group has from 1 to 16 carbon atoms and which may be partially substituted by further groups, preferably by F, Cl, Br, $NO_2$, CN, alkyl, aryl or heterocyclic aryl,
an aryl radical, which may be partially substituted by further groups, preferably by F, Cl, Br, $NO_2$, CN, alkyl, aryl or heterocyclic aryl, or
an aromatic heterocyclic radical, which may be partially substituted by further groups, preferably by F, Cl, Br, $NO_2$, CN, alkyl, aryl or heterocyclic aryl,
where one, two or three $CH_2$ groups in an alkyl radical may have been replaced by identical or different heteroatoms, preferably O, NH or N(alkyl) having from 1 to 6 carbon atoms,
and where all three R radicals cannot simultaneously be perfluorinated or perchlorinated.

After the reaction, the perfluoroalkanesulfonic acid salt formed precipitates or can be isolated by conventional methods. The unreacted alkyl perfluoroalkanesulfonate merely has to be distilled off.

This subsequent reaction with the ester is preferably carried out using a compound $XR^1R^2R^3$ which is selected from the group consisting of $$X(C_2H_5)_3, X(C_3H_7)_3, X(C_4H_9)_3,$$

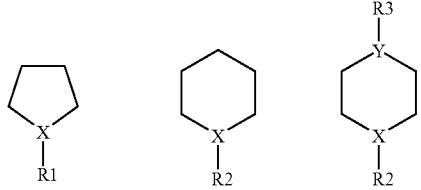

where
X and Y are P or N,
$R^1$ $R^2$
and $R^3$ are H, alkyl, preferably having from 1 to 16 carbon atoms, alkylaryl, aryl or heterocyclic aryl,
where one, two or three $CH_2$ groups in the ring and/or in the alkyl radical may have been replaced by identical or different heteroatoms, preferably O, NH or N(alkyl) having from 1 to 6 carbon atoms, and where the ring and/or the alkyl radical may have been partially substituted by further groups, preferably by F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ where $1 \leq n \leq 6$ and $0 \leq x \leq 2n+1$, alkylaryl, aryl, heterocyclic aryl or heterocyclic alkylaryl.

Preference is furthermore given to the reaction of a perfluoroalkanesulfonic acid ester obtained in accordance with the invention with a compound $XR^1R^2R^3$ selected from the following group to give a salt:

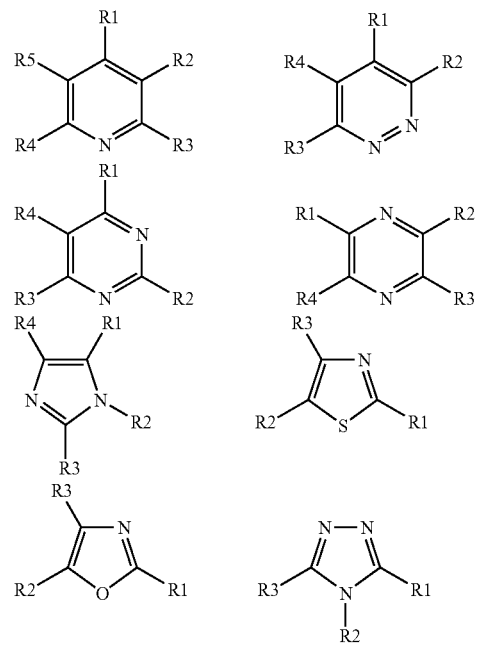

where $R^1$ to $R^4$ are identical or different, are optionally linked directly to one another by a single or double bond and are each, individually or together,
hydrogen,
a halogen, preferably fluorine,
with the proviso that there is no N-halogen bond,
an alkyl radical having from 1 to 8 carbon atoms, which may be partially or fully substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ where $1 \leq n \leq 6$ and $0 \leq x \leq 2n+1$, alkylaryl, aryl or heterocyclic aryl,
an aryl radical,
an alkylaryl radical,
an aromatic heterocyclic radical,
a heterocyclic alkylaryl radical.

The compounds containing perfluoroalkanesulfonic acid radicals which have been prepared in accordance with the invention, i.e. the perfluoroalkanesulfonic acid esters and in particular the salts thereof, can be employed in electrolytes, electrochemical cells, primary and secondary batteries, capacitors and/or super- or ultracapacitors, for example as solvents or conductive salts. The salts here can be employed as conductive salts either in pure form or alternatively in the form of their mixtures. It is also possible to use the salts as conductive salt together with further salts known to the person skilled in the art. In addition, the perfluoroalkanesulfonic acid esters are strong alkylating agents and are suitable for the alkylation of organic compounds, for example in the preparation of medicaments and crop protection agents.

The compounds containing perfluoroalkanesulfonic acid radicals according to the invention, in particular the salts, can be used in liquid, gelatinous, polymeric or solid electrolytes. To this end, mixtures comprising the conductive salts and suitable polymers and/or suitable solvents can be employed. For the purposes of the present invention, the term mixture covers pure mixtures of the components, mixtures in which the salt(s) is (are) included in a polymer or gel, and mixtures in which chemical and/or physical bonds exist between the salt(s) and a polymer or gel. In the case of a gelatinous electrolyte, the mixture preferably comprises a suitable solvent in addition to the salt(s) and the polymer.

The solvents employed for liquid or gelatinous electrolytes are particularly preferably aprotic solvents or mixtures thereof which are suitable for use in primary or secondary batteries, capacitors, supercapacitors or electrochemical cells, for example carbonates, esters, ethers, sulfolanes or nitriles, such as, for example, dimethyl carbonate, diethyl carbonate, butylene carbonate, propylene carbonate, ethylene carbonate, ethyl methyl carbonate, methyl propyl carbonate, 1,2-dimethoxyethane, 1,2-diethoxyethane, methyl acetate, γ-butyrolactone, ethyl acetate, methyl propionate, ethyl propionate, methyl butyrate, ethyl butyrate, dimethyl sulfoxide, dioxolane, sulfolane, acetonitrile, acrylonitrile, tetrahydrofuran, 2-methyltetrahydrofuran or mixtures thereof.

The polymers employed for polymeric or gelatinous electrolytes are preferably homopolymers or copolymers of acrylonitrile, vinylidene difluoride, methyl (meth)acrylate, tetrahydrofuran, ethylene oxide, siloxane, phosphazene or a mixture of at least two of the above-mentioned homopolymers and/or copolymers, it being possible for the polymers to be at least partially crosslinked.

The complete disclosure content of all applications, patents and publications mentioned above and below, and of the corresponding application DE 101 63 458.7, filed on 21 Dec. 2001, is incorporated into this application by way of reference.

Even without further comments, it is assumed that a person skilled in the art will be able to utilise the above description in its broadest scope. The preferred embodiments and examples should therefore merely be regarded as descriptive disclosure which is absolutely not limiting in any way.

All NMR spectra were measured on a Bruker WP 80 SY spectrometer ($^1$H: 80.1 MHz, $^{19}$F: 75.5 MHz).

EXAMPLE 1

19.4 g (0.129 mol) of trifluoromethanesulfonic acid are introduced into a round-bottomed flask fitted with a reflux condenser. 5.81 g (0.0646 mol) of dimethyl carbonate are added with constant stirring and cooling using an ice bath. The reaction mixture is subsequently heated at 90° C. for 3 hours using an oil bath (temperature in the oil bath) until the evolution of gas ceases. After the cooling to room temperature, the reaction mixture is distilled at atmospheric pressure. 12.3 g of a transparent, colourless liquid are isolated (boiling range 100-102° C.). This mixture comprises 96.3% of methyl trifluoromethanesulfonate (methyl triflate) and 3.7% of dimethyl carbonate. The yield of methyl triflate is 55.8%.

$^{19}$F-NMR, ppm (solvent: CDCl$_3$, internal standard: CCl$_3$F): −74.86 s (CF$_3$)

$^1$H-NMR, ppm (solvent: CDCl$_3$, internal standard: TMS): 4.21 q; $J^5_{H,F}$=0.7 Hz $^{19}$F- and $^1$H-NMR data correspond to the literature data for methyl triflate (Encyclopedia of Reagents for Organic Synthesis, Editor in Chief Leo A. Paquette, Vol. 5, John Wiley and Sons Ltd., 1995, 3618; J. Org. Chem., Vol. 38, No. 21, 1973, 3673-3677)

EXAMPLE 2

76.36 g (0.509 mol) of trifluoromethanesulfonic acid are introduced into a round-bottomed flask fitted with a reflux condenser. 71.60 g (0.509 mol) of benzoyl chloride are added over the course of 2 minutes with constant stirring. During this addition, the mixture warms, and gas evolution is observed. Without cooling the reaction mixture, 45.81 g (0.509 mol) of dimethyl carbonate are added, and the reaction mixture is subsequently heated at 90° C. for 10 hours using an oil bath (temperature in the oil bath). After cooling to room temperature, the reaction mixture is distilled at atmospheric pressure, giving 75.05 g (89.9%) of methyl trifluoromethanesulfonate (methyl triflate) as a transparent, colourless liquid (boiling range 98-99° C.).

$^{19}$F- and $^1$H-NMR data for the methyl triflate correspond to the literature data and the data indicated in Example 1.

A further 49.15 g (0.328 mol) of trifluoromethanesulfonic acid, 46.10 g (0.328 mol) of benzoyl chloride and 29.49 g (0.328 mol) of dimethyl carbonate are added to the distillation residue with stirring. The reaction mixture is subsequently heated at 90° C. using an oil bath (temperature in the oil bath) for 6 hours, giving 52.00 g (yield: 96.8%) of pure methyl triflate by distillation.

The average yield of methyl triflate in the two successive reactions is 92.6%.

After isolation of the methyl triflate, the reaction mixture which remains is distilled under reduced pressure (boiling range: 89-91° C. at 2.7 kPa), giving 94.92 g (83.4%) of pure methyl benzoate.

$^1$H-NMR, ppm (solvent: CD$_3$CN, internal standard: TMS): 3.86 s (CH$_3$), 7.52 m (3H), 8.00 m (2H).

The distillation residue remaining after distillation of the liquids is benzoic acid, which can be crystallised from ethanol/water (melting point 121-122° C.).

EXAMPLE 3

29.77 g (0.160 mol) of p-nitrobenzoyl chloride, 15.00 g (0.167 mol) of dimethyl carbonate and 24.07 g (0.160 mol) of trifluoromethanesulfonic acid are mixed in a round-bottomed flask fitted with a reflux condenser and heated at about 75° C. for 2 hours in an oil bath (temperature in the oil bath) with constant stirring. After cooling to room temperature, the methyl triflate is distilled off under atmospheric pressure, giving 18.57 g (yield: 70.6%) of a transparent, colourless liquid (boiling range 98-99° C.).

The solid distillation residue which remains consists principally of methyl p-nitro-benzoate, which is obtained as a pale-yellow product after crystallisation from methanol (25.0 g, yield: 86.0%, melting point: 93-94° C.).

EXAMPLE 4

20.84 g (0.139 mol) of trifluoromethanesulfonic acid are introduced into a round-bottomed flask fitted with a reflux condenser. 24.69 g (0.139 mol) of 2,6-difluorobenzoyl chloride and 12.50 g (0.139 mol) of dimethyl carbonate are added with constant stirring and with ice cooling. The ice bath is replaced by an oil bath, and the reaction mixture is heated at 80-110° C. for 4 hours (temperature in the oil bath)

with stirring. Gas evolution commences at about 70° C. After completion of the reaction, the mixture is cooled to room temperature, and the methyl triflate is distilled off under atmospheric pressure, giving 20.63 g (yield: 90.6%) of a transparent, colourless liquid (boiling range 98-99° C.).

The reaction mixture which remains is distilled under reduced pressure (boiling point: 90° C. at 2.0 kPa), giving 21.50 g (yield: 89.4%) of pure methyl 2,6-difluorobenzoate.

$^{19}$F-NMR, ppm (solvent: $CD_3CN$, internal standard: $CCl_3F$): −111.50 t (2F), $J_{H,F}$=7.0 Hz $^1$H-NMR, ppm (solvent: $CD_3CN$, internal standard: TMS): 3.92 s ($CH_3$), 7.04 m (2H), 7.53 m (1H)

EXAMPLE 5

16.08 g (0.107 mol) of trifluoromethanesulfonic acid are introduced into a round-bottomed flask fitted with a reflux condenser. 24.72 g (0.107 mol) of pentafluorobenzoyl chloride and 9.65 g (0.107 mol) of dimethyl carbonate are added with constant stirring and with ice cooling. The ice bath is replaced by an oil bath, and the reaction mixture is heated at 80-110° C. for 4 hours (temperature in the oil bath) with stirring. Gas evolution commences at about 75° C. After completion of the reaction, the mixture is cooled to room temperature, and the methyl triflate is distilled off under atmospheric pressure, giving 14.81 g (yield: 84.2%) of a transparent, colourless liquid (boiling range 98-99° C.).

The reaction mixture which remains is distilled under reduced pressure (boiling point: 72° C. at 2.0 kPa), giving 21.45 g (yield: 79.7%) of pure methyl pentafluorobenzoate.

$^{19}$F-NMR, ppm (solvent: $CD_3CN$, internal standard: $CCl_3F$): −139.58 dm (2F), −150.37 tt (1F), −161.89 m (2F), $J^3_{F,F}$=20.0 Hz, $J^4_{F,F}$=4.4 Hz $^1$H-NMR, ppm (solvent: $CD_3CN$, internal standard: TMS): 3.96 s ($CH_3$)

EXAMPLE 6

4.23 g (0.0187 mol) of benzoic anhydride and 2.53 g (0.0187 mol) of dimethyl carbonate are introduced into a round-bottomed flask fitted with a reflux condenser. 2.81 g (0.0187 mol) of trifluoromethanesulfonic acid are added with constant stirring and with ice cooling. The ice bath is replaced by an oil bath, and the reaction mixture is heated at 90-110° C. for 4 hours (temperature in the oil bath) with stirring until the evolution of gas ceases. After completion of the reaction, the mixture is cooled to room temperature, and the methyl triflate is distilled off under atmospheric pressure, giving 0.55 g (yield: 17.9%) of a transparent, colourless liquid (boiling range 99-100° C.).

The reaction mixture which remains is distilled under reduced pressure (boiling range: 88-93° C. at 2.0 kPa), giving 3.96 g (yield: 77.8%) of virtually pure methyl benzoate.

$^1$H-NMR, ppm (solvent: $CD_3CN$, internal standard: TMS): 3.86 s ($CH_3$), 7.52 m (3H), 8.00 m (2H)

EXAMPLE 7

10.73 g (0.0578 mol) of p-nitrobenzoyl chloride and 6.84 g (0.0579 mol) of diethyl carbonate are introduced into a round-bottomed flask fitted with a reflux condenser. 8.68 g (0.0579 mol) of trifluoromethanesulfonic acid are added with constant stirring and with ice cooling. The ice bath is replaced by an oil bath, and the reaction mixture is heated at 100-110° C. for 5 hours (temperature in the oil bath) with stirring until the evolution of gas ceases. After completion of the reaction, the mixture is cooled to room temperature, and the ethyl trifluoromethanesulfonate (ethyl triflate) is distilled off under atmospheric pressure, giving 3.28 g (yield: 31.8%) of a transparent, colourless liquid (boiling range 114-116° C.).

$^{19}$F-NMR, ppm (solvent: $CDCl_3$, internal standard $CCl_3F$): −75.68 s ($CF_3$)

$^1$H-NMR, ppm (solvent: $CDCl_3$, internal standard TMS): 1.51 t ($CH_3$), 4.62 q ($CH_2$), $J^3_{H,H}$=7.0 Hz $^{19}$F- and $^1$H-NMR data correspond to the literature data for ethyl trifluoromethanesulfonate (ethyl triflate) (Eur. Polym. J., Vol. 16, No. 9, 1980, 861-865).

EXAMPLE 8

13.67 g (0.0911 mol) of trifluoromethanesulfonic acid are introduced at −30° C. into a round-bottomed flask fitted with a reflux condenser. 12.80 g (0.0911 mol) of benzoyl chloride are added over the course of 2 minutes with constant stirring, during which the mixture warms slightly. 10.77 g (0.0912 mol) of diethyl carbonate are then added without cooling the mixture. The reaction mixture is heated at 70-90° C. for 4.5 hours in an oil bath (temperature in the oil bath) with stirring. Gas evolution commences at an oil-bath temperature of about 70° C. After completion of the reaction, the mixture is cooled to room temperature, and the ethyl trifluoromethanesulfonate (ethyl triflate) is distilled off under atmospheric pressure, giving 13.10 g (yield: 80.8%) of a transparent, colourless liquid (boiling point 115° C.).

$^{19}$F- and $^1$H-NMR data for the ethyl triflate correspond to the literature data (cf. also Example 7).

The reaction mixture which remains is distilled under reduced pressure (boiling point: 100° C. at 2.0 kPa). 9.91 g (yield: 72.5%) of pure ethyl benzoate are obtained.

$^1$H-NMR, ppm (solvent: $CD_3CN$, internal standard: TMS): 1.35 t (3H, $CH_3$), 4.33 q (2H, $CH_2$), 7.53 m (3H), 8.00 m (2H), $J^3_{H,H}$=7.0 Hz $^1$H-NMR data correspond to the literature data for ethyl benzoate (The Aldrich Library of NMR Spectra, Edition II, Charles J Pouchert, Volume 2, 281)

EXAMPLE 9

17.74 g (0.1182 mol) of trifluoromethanesulfonic acid are introduced into a round-bottomed flask fitted with a reflux condenser. 21.41 g (0.1177 mol) of trichloroacetyl chloride are added over the course of 2 minutes with constant stirring. 10.60 g (0.1177 mol) of dimethyl carbonate are then added over the course of 5 minutes without cooling the mixture. The reaction mixture warms slightly and is heated at 80-100° C. for 7 hours in an oil bath (temperature in the oil bath) with stirring until the evolution of gas ceases. After cooling to room temperature, the mixture is distilled under atmospheric pressure, giving 17.48 g (yield: 90.5%) of methyl trifluoromethanesulfonate as a transparent, colourless liquid (boiling range 98-100° C.).

$^{19}$F- and $^1$H-NMR data correspond to the literature data and those in the preceding examples.

The reaction mixture which remains is distilled further (boiling range: 152-153° C.). 15.16 g (yield: 72.6%) of methyl trichloroacetate are obtained.

$^1$H-NMR, ppm (solvent: $CD_3CN$, internal standard: TMS): 3.98 s ($CH_3$)

EXAMPLE 10

6.31 g (0.0768 mol) of 1-methylimidazole in 50 ml of dry hexane are introduced into a round-bottomed flask fitted with a reflux condenser. 13.75 g (0.0772 mol) of ethyl triflate are added over the course of 20 minutes with constant stirring and cooling with the aid of an ice bath. After a further 10 minutes, the ice bath is then replaced by an oil bath, and the reaction mixture is refluxed for one hour (oil-bath temperature 70-75° C.). After the hexane has been removed by distillation, the reaction mixture which remains is held at 80-90° C. in a 30-100 Pa vacuum for 5 hours, giving 19.80 g (yield: 99.1%) of 1-methyl-3-ethylimidazolium trifluoromethanesulfonate as a transparent, colourless liquid.

$^{19}$F-NMR, ppm (solvent: CD$_3$CN, internal standard CCl$_3$F): −78.05 s (CF$_3$SO$_3^-$)

$^1$H-NMR, ppm (solvent: CD$_3$CN, internal standard TMS): 1.48 t (CH$_3$), 3.89 s (CH$_3$), 4.23 q (CH$_2$), 7.47 dd (1H), 7.54 dd (1H), 8.74 br.s. (1H), J$^3_{H,H}$=1.8 Hz

EXAMPLE 11

141.13 g (1.657 mol) of 1-methylpyrrolidine in 800 ml of dry hexane are introduced into a round-bottomed flask fitted with a reflux condenser. 272 g (1.657 mol) of methyl triflate are added over the course of 45 minutes with constant stirring and cooling with the aid of an ice bath. The ice bath is then replaced by an oil bath, and the reaction mixture is refluxed for 15 minutes (oil-bath temperature 70-75° C.). After cooling to room temperature, the white precipitate is filtered off, washed twice with 100 ml of hexane and dried at 110° C. under a 30-100 Pa vacuum for three hours, giving 409 g (yield: 99.1%) of 1,1-dimethylpyrrolidinium trifluoromethanesulfonate as a white solid.

$^{19}$F-NMR, ppm (solvent: CD$_3$CN, internal standard CCl$_3$F): −78.00 s (CF$_3$SO$_3^-$)

$^1$H-NMR, ppm (solvent: CD$_3$CN, internal standard TMS): 2.17 m (4H), 3.07 s (CH$_3$), 3.45 m (4H)

EXAMPLE 12

5.77 g (0.0505 mol) of 1,4-dimethylpiperazine in 70 ml of dry hexane are introduced into a round-bottomed flask fitted with a reflux condenser. 16.56 g (0.1009 mol) of methyl triflate are added over the course of 20 minutes with constant stirring and cooling with the aid of an ice bath. The ice bath is then replaced by an oil bath, and the reaction mixture is refluxed for 15 minutes (oil-bath temperature 70-75° C.). After cooling to room temperature, the white precipitate is filtered off, washed twice with 10 ml of hexane and dried at 80° C. under a 30-100 Pa vacuum for three hours, giving 20.68 g (yield: 92.7%) of 1,1,4,4-tetramethyl-piperazinium di(trifluoromethanesulfonate) as a white solid.

$^{19}$F-NMR, ppm (solvent: (CD$_3$)$_2$SO$_2$, internal standard CCl$_3$F): −77.40 s (CF$_3$SO$_3^-$)

$^1$H-NMR, ppm (solvent: (CD$_3$)$_2$SO$_2$, internal standard TMS): 3.30 s (4CH$_3$), 3.82 s (4CH$_2$)

All $^{19}$F- and $^1$H-NMR spectra were recorded on a BrukerWP 80 SY spectrometer (80.1 MHz for $^1$H and 75.4 MHz for $^{19}$F).

The invention claimed is:

1. A process for the preparation of a compound containing a perfluoroalkanesulfonic acid radical, comprising reacting a perfluoroalkanesulfonic acid-directly with dialkyl carbonate, wherein a water or alcohol consuming reagent is optionally present, to give alkyl perfluoroalkanesulfonate or to give alkyl perfluoroalkanesulfonate and a carboxylic acid ester.

2. A process according to claim 1, wherein a perfluoroalkanesulfonic acid is reacted directly with a dialkyl carbonate in the presence of a water or alcohol consuming reagent to give an alkyl perfluoroalkanesulfonate or to give an alkyl perfluoroalkanesulfonate and a carboxylic acid ester.

3. A process according to claim 1, wherein the dialkyl carbonate is dimethyl carbonate, diethyl carbonate, dipropyl carbonate, dibutyl carbonate, methyl ethyl carbonate or a mixture of these dialkyl carbonates.

4. A process according to claim 1, wherein the carboxylic acid derivative is carboxylic acid halide, carboxylic anhydride or mixed carboxylic/sulfonic anhydride.

5. A process according to claim 4, wherein the carboxylic acid halide is benzoyl chloride, p-nitrobenzoyl chloride, 2,6-difluorobeuzoyl chloride, pentafluorobenzoyl chloride, 2-chlorobenzoyl chloride, 3-chlorobenzoyl chloride, 4-chlorobenzoyl chloride, 2-bromobenzoyl chloride, 3-bromobenzoyl chloride, 4-bromobenzoyl chloride, 2,3-dichlorobenzoyl chloride, 2,4-dichlorobenzoyl chloride, 2,6-dichlorobenzoyl chloride, 3,4-dichlorobenzoyl chloride, 3,5-dichlorobenzoyl chloride or trichloroacetyl chloride.

6. A process according to claim 4, wherein the carboxylic anhydride is benzoic anhydride, 2,2'-dichlorobenzoic anhydride, 3,3t-dichlorobenzoic anhydride, 4,4'-dichlorobenzoic anhydride, 2,2',3,3'-tetrachlorobenzoic anhydride, 2,2',4,4'-tetrachlorobenzoic anhydride, 2,2',6,6'-tetrachlorobenzoic anhydride, 3,3',4,4'-tetrachlorobenzoic anhydride, 3,3', 5,5'-tetrachlorobenzoic anhydride, 2-bromobenzoic anhydride, 3-bromobenzoic anhydride, 4-bromobenzoic anhydride or 2,2',6,6'-tetrafluorobenzoic anhydride.

7. A process according to claim 1, carried out at a temperature of between room temperature and 150° C.

8. A process according to claim 1, wherein the reaction time is between 1 and 10 hours.

9. A process for the preparation of a compound containing a perfluoroalkanesulfonic acid radical, comprising reacting an alkyl perfluoroalkanesulfonate prepared in accordance with claim 1 with a compound of the formula XR$^1$R$^2$R$^3$ where X is P or N, and R$^1$, R$^2$ and R.$^3$ are identical or different, are optionally linked directly to one another by a single or double bond and are each, individually or together, hydrogen, an alkyl radical having from 1 to 16 carbon atoms, which may be partially or fully substituted by further groups, an alkylaryl radical whose alkylene group has from 1 to 16 carbon atoms and which may be partially substituted by further groups, an aryl radical, which may be partially substituted, or an aromatic heterocyclic radical, which may be partially substituted by further groups, preferably F, Cl, Br, NO$_2$, CN, alkyl, aryl or heterocyclic aryl, where one, two or three CH$_2$ groups in an alkyl radical may have been replaced by identical or different heteroatoms, and where all three R radicals cannot simultaneously be perfluorinated or perchlorinated.

10. A process according to claim 1, where said water or alcohol consuming reagent is a carboxylic acid derivative whose organic radical is stable to perfluoroalkanesulfonic acid.

11. A process according to claim 7, carried out at a temperature of between 50 and 110° C.

12. A process according to claim 8, wherein the reaction time is between 2 and 5 hours.

13. A process according to claim 9, wherein the alkyl radical having from 1 to 16 carbon atoms may be partially or fully substituted by F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$ where $1 \leq n \leq 6$ and $0 \leq x \leq 2n+1$.

14. A process according to claim 9, wherein the alkylaryl radical whose alkylene group has from 1 to 16 carbon atoms and which may be partially substituted by F, Cl, Br, $NO_2$, CN, alkyl, aryl or heterocyclic aryl.

15. A process according to claim 9, wherein the aryl radical, which may be partially substituted by F, Cl, Br, $NO_2$, CN, alkyl, aryl or heterocyclic aryl.

16. A process according to claim 9, wherein the identical or different heteroatoms are O, NH or N(alkyl) having from 1 to 6 carbon atoms.

17. A process according to claim 2, where said water or alcohol consuming reagent is a carboxylic acid derivative whose organic radical is stable to perfluoroalkanesulfonic acid.

* * * * *